US008847885B2

(12) United States Patent
Huang

(10) Patent No.: US 8,847,885 B2
(45) Date of Patent: Sep. 30, 2014

(54) ELECTRONIC DEVICE AND METHOD FOR RELIEVING VISUAL FATIGUE USING THE ELECTRONIC DEVICE

(71) Applicant: FIH (Hong Kong) Limited, Kowloon (HK)

(72) Inventor: Hsiu-Wen Huang, New Taipei (TW)

(73) Assignee: FIH (Hong Kong) Limited, Kowloon (HK)

( * ) Notice: Subject to any disclaimer, the term of this patent is extended or adjusted under 35 U.S.C. 154(b) by 80 days.

(21) Appl. No.: 13/674,157

(22) Filed: Nov. 12, 2012

(65) Prior Publication Data

US 2013/0169523 A1    Jul. 4, 2013

(30) Foreign Application Priority Data

Dec. 30, 2011    (TW) .............................. 100149932 A

(51) Int. Cl.
*G09G 5/00*    (2006.01)
*G06F 9/44*    (2006.01)
*G06F 3/01*    (2006.01)
*G06F 19/00*    (2011.01)

(52) U.S. Cl.
CPC .............. *G06F 3/013* (2013.01); *G06F 9/4446* (2013.01); *G06F 19/3406* (2013.01)
USPC ........................................................ 345/156

(58) Field of Classification Search
None
See application file for complete search history.

(56) References Cited

U.S. PATENT DOCUMENTS

| 2006/0256083 A1* | 11/2006 | Rosenberg ..................... 345/156 |
| 2012/0256967 A1* | 10/2012 | Baldwin et al. ............... 345/684 |
| 2013/0027302 A1* | 1/2013 | Iwaizumi et al. ............. 345/158 |
| 2013/0342309 A1* | 12/2013 | Jiang .............................. 340/3.1 |

* cited by examiner

*Primary Examiner* — Adam R Giesy
(74) *Attorney, Agent, or Firm* — Novak Druce Connolly Bove + Quigg LLP

(57) ABSTRACT

An electronic device includes a visual sensor and a display screen. The visual sensor senses whether a user is looking at the display screen. If the user is looking at the display screen, the electronic device adjusts a font size of a font being displayed on the display screen. If the user looks at the display screen for not less than a first predefined time, the electronic device prompts the user to have a rest and turn off the display screen. After the electronic device has been turned off for more than a second predefined time, the display screen is turned on again automatically.

15 Claims, 3 Drawing Sheets

ELECTRONIC DEVICE AND METHOD FOR RELIEVING VISUAL FATIGUE USING THE ELECTRONIC DEVICE

BACKGROUND

1. Technical Field

Embodiments of the present disclosure relate to electronic device systems and methods, and particularly to an electronic device and a method for relieving visual fatigue using the electronic device.

2. Description of Related Art

Many electronic devices (mobile phones, and tablet computers for example) provide a display screen for a user to browse the internet. However, for small display screens when the user wants to view an entire web page, the font sizes of the web page may be too small, and the user may develop eye strain when reading such pages for an extended period of time. This is unhealthy. Also, the fonts may be so small the user may not be able to discern the words on the pages.

DETAILED DESCRIPTION

The disclosure, including the accompanying drawings, is illustrated by way of examples and not by way of limitation. It should be noted that references to "an" or "one" embodiment in this disclosure are not necessarily to the same embodiment, and such references mean "at least one."

In general, the word "module," as used herein, refers to logic embodied in hardware or firmware, or to a collection of software instructions, written in a programming language. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable media may include CDs, DVDs, BLU-RAY, flash memory, and hard disk drives.

Figure 1:
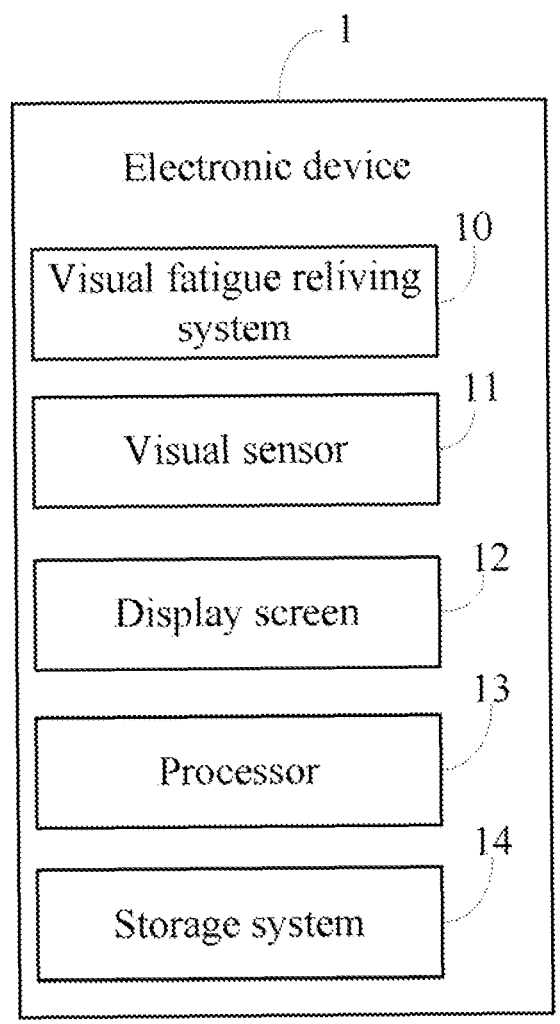
FIG. 1 is a block diagram of one embodiment of an electronic device including a visual fatigue relieving system.

FIG. 1 is a block diagram of one embodiment of an electronic device 1 including a visual fatigue reliving system 10, a visual sensor 11 and a display screen 12. In some embodiments, the electronic device 1 may be a mobile phone, or a tablet computer, for example. The visual sensor 11 senses whether or not the eyes of a user are looking at the display screen 12. In one embodiment, the display screen 12 may be a touch screen.

In an exemplary embodiment, the electronic device 1 includes at least one processor 13 and a storage system 14. In one embodiment, the storage system 14 may be a magnetic storage system, an optical storage system, or other suitable storage medium. The storage system 14 stores a plurality of images as models or examples of human eyes (eyes models). The eyes models may include different directions in which the eyes of the human may be looking. The visual sensor 11 detects whether the eyes of the user are looking at the display screen 12 according to the eyes models. The storage system 14 also stores a preset font size for web pages or other pages displayed on the display screen 12. The font size of the words on the pages can be according to user's requirements, such as 10 or 12 font sizes.

Figure 2:
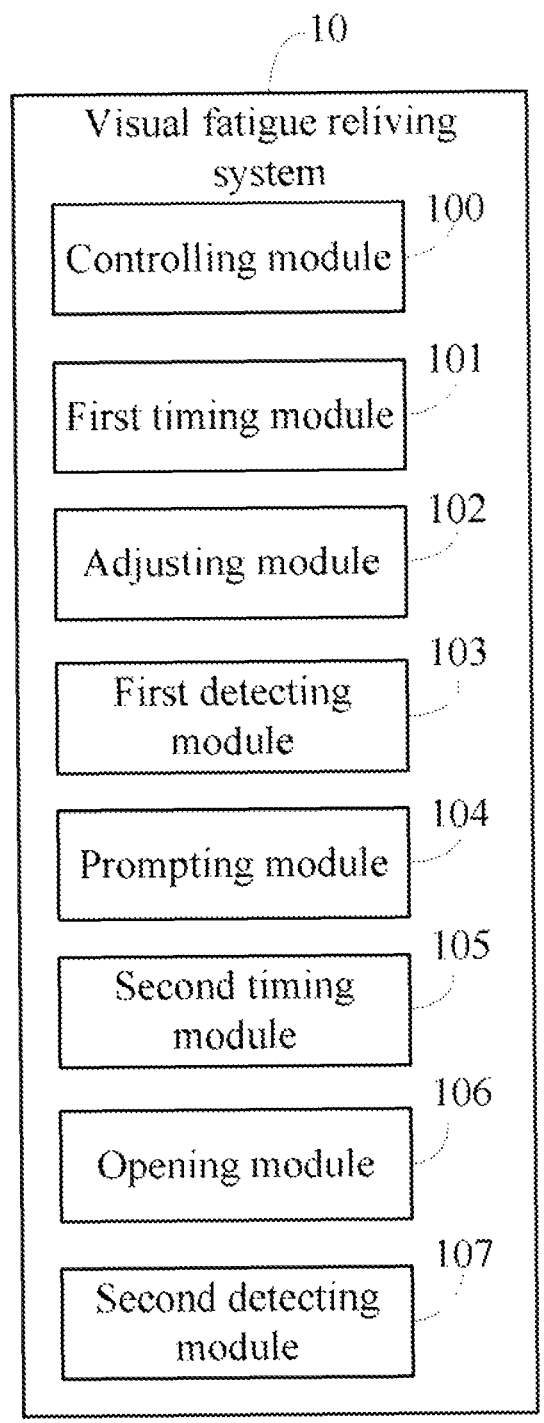
FIG. 2 is a block diagram of one embodiment of function modules of the visual fatigue relieving system in FIG. 1.

As shown in FIG. 2, the visual fatigue relieving system 10 includes a controlling module 100, a first timing module 101, an adjusting module 102, a first detecting module 103, a prompting module 104, a second timing module 105, an opening module 106, and a second detecting module 107. The one or more modules may comprise computerized instructions in the form of one or more programs that are stored in the storage system 14 and executed by the at least one processor 13 to provide functions of the electronic device 1.

The controlling module 100 controls the visual sensor 11 to detect whether the user looks at the display screen 12. In one embodiment, the visual sensor 11 captures an image of the eyes in a predefined range. The controlling module 100 determines whether the image of the eyes matches one of the eyes models in the storage system 14. If the image of the eyes matches one of the eyes models, the controlling module 100 determines that the user is looking at the display screen 12. If no eyes model matches the image of the eyes, the controlling module 100 determines that the user is not looking at the display screen 12.

If the user looks at the display screen 12, the first timing module 101 sets an initial time. In one embodiment, the initial time can be set as a system time of the electronic device 1, such as 2 seconds, for example.

The adjusting module 102 adjusts a font size of the font of a page being displayed on the display screen 12 to the preset font size. In one embodiment, when the user browsers a webpage, the adjusting module 102 adjusts the font size of the font of the webpage to the preset font size.

The first detecting module 103 detects a reading time of the eyes by calculating a time difference between a current system time of the electronic device 1 and the initial time, and determines whether the user keeps looking at the screen 12 for not less than a first predefined time according to the reading time of the eyes. In one embodiment, the reading time of the eyes is defined as a time period indicating that the user keeps looking at the display screen 12. The first predefined time is healthy for the eyes of the user, and may be set as 20 minutes. If the reading time of the eyes continues for not less than the first predefined time, the first detecting module 103 determines that the user is looking at the screen 12 for not less than the first predefined time.

As soon as the user has been looking at the screen 12 for not less than the first predefined time, the prompting module 104 prompts the user to have a rest, and then controls the display screen 12 to automatically turn off. In one embodiment, the prompting module 104 provides a dialog box to inform him/her that he/she has been looking at the display screen 12 for not less than the first predefined time.

The second timing module 105 detects whether the display screen 12 has been turned off for more than a second predefined time. In one embodiment, the second predefined time may be 20 seconds.

If the display screen 12 has been turned off for more than the second predefined time, the opening module 106 controls the display screen 12 to automatically turn on. The user can use the display screen 12 again in the normal way after the display screen 12 is turned on again.

If the display screen 12 has been turned off not more than the second predefined time, the second detecting module 107 detects whether the user has manually turned on the display screen 12 manually. If the user has turned on the display screen 12 manually, the first timing module 101 sets a new initial time. If the user has not opened the display screen 12 manually, the display screen 12 continues to be turned off.

Figure 3:
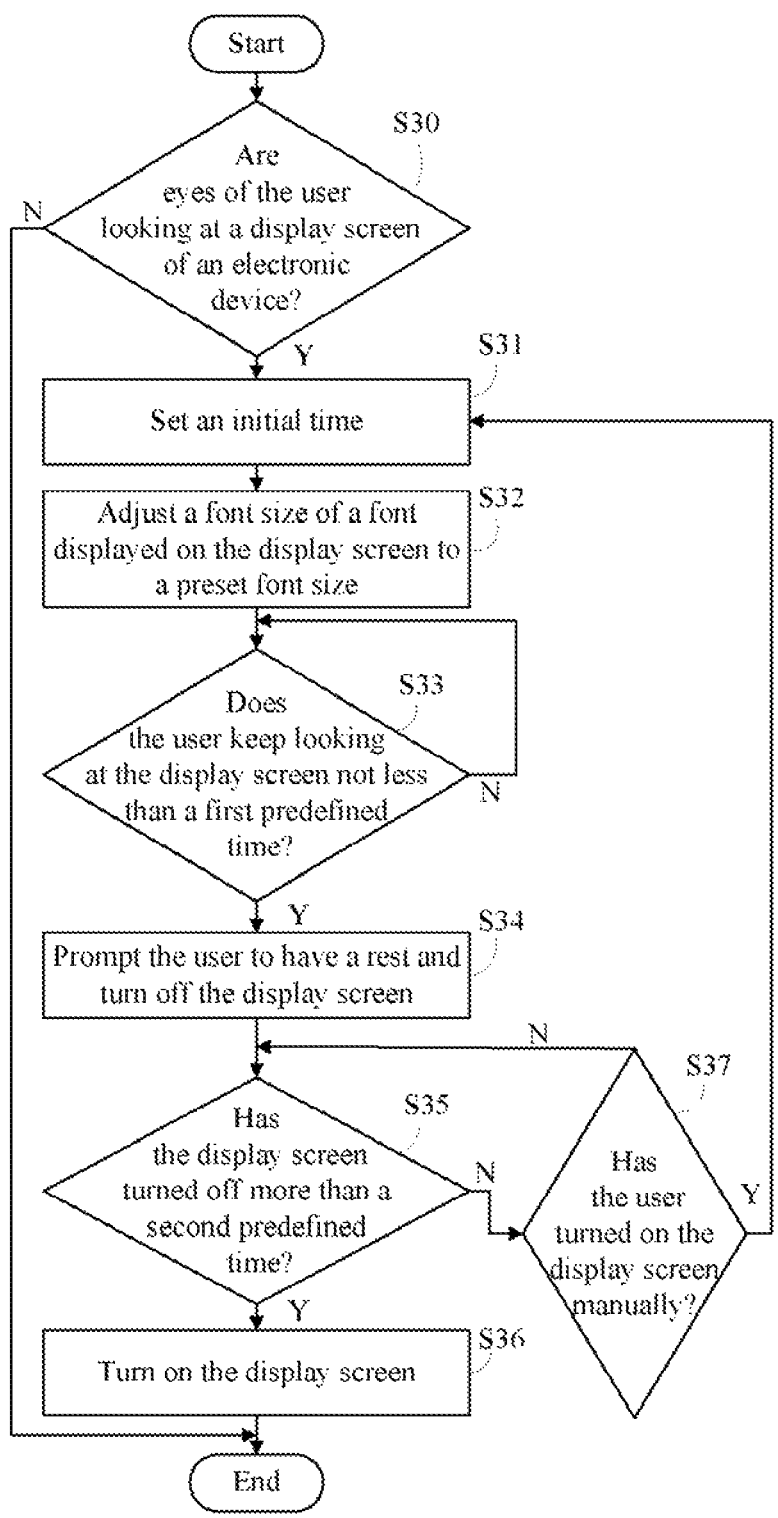
FIG. 3 is a flowchart illustrating one embodiment of a method for relieving visual fatigue using an electronic device.

FIG. 3 is a flowchart illustrating a method for relieving visual fatigue using the electronic device 1 of FIG. 1. Depending on the embodiment, additional steps may be increased, others removed, and the ordering of the steps may be changed.

In step S30, the controlling module 100 controls the visual sensor 11 to detect whether the user is looking at the display screen 12. If the user is looking at the display screen 12, step S31 is implemented. Otherwise, step S30 is repeated.

In step S31, the first timing module 101 sets an initial time. The initial time is set as a present system time of the electronic device 1.

In step S32, the adjusting module 102 adjusts a font size of a font on a page displayed on the display screen 12 to the preset font size.

In step S33, the first detecting module 103 detects a reading time of the eyes by calculating a time difference between a current system time of the electronic device 1 and the initial time, to determine whether the user has been reading at the display screen 12 for not less a first predefined time. If the user keeps looking at the display screen 12 for not less than the first predefined time, block S34 is implemented. If the time difference between the current system time and the initial time is less than the first predefined time, the reading time of the eyes is determined less than the first predefined time. Step S33 is repeated as long as the first detecting module 103 keeps detecting the reading time of the eyes is less than the first predefined time. If the first detecting module 103 detects that the reading time of the eyes is qual to or more than the first predefined time, the procedure goes to step S34.

In step S34, the prompting module 104 prompts the user to have a rest, and controls the display screen 12 to automatically turn off.

In step S35, the second timing module 105 detects whether the display screen 12 has been turned off for more than a second predefined time. As soon as the period of the display screen 12 being turned off exceeds the second predefined time, step S36 is implemented. Until the second predefined time is reached, while the display screen 12 is turned off, step S37 is implemented.

In step S36, the opening module 106 turns on the display screen 12 again automatically for the user to resume looking.

In step S37, the second detecting module 107 detects whether the user has turned on the display screen 12 manually. If the user has manually turned on the display screen 12, step S31 is repeated. If the user does not turn on the display screen 12 manually, step S35 is repeated.

Although certain inventive embodiments of the present disclosure have been specifically described, the present disclosure is not to be construed as being limited thereto. Various changes or modifications may be made to the present disclosure without departing from the scope and spirit of the present disclosure.

What is claimed is:

1. An electronic device, comprising:
    a storage system;
    at least one processor; and
    one or more programs stored in the storage system and executed by the at least one processor, the one or more programs comprising:
    a controlling module that controls a visual sensor of the electronic device to capture an image of eyes of a user, and detects whether the user is looking at a display screen of the electronic device by determining whether the image of the eyes matches an eyes model stored in the storage system;
    an adjusting module that adjusts a font size of a font on a page displayed on the display screen to a preset font size when the user is looking at the display screen; and
    a prompting module that prompts the user to have a rest and controls the display screen to turn off when the user has looked at the display screen not less than a first predefined time.

2. The electronic device as described in claim 1, wherein the controlling module determines that the user is looking at the display screen when the image of the eyes matches one of the eyes models.

3. The electronic device as described in claim 1, wherein the one or more programs further comprise a first timing module that sets an initial time when the visual sensor determines that the user is looking at the screen.

4. The electronic device as described in claim 1, wherein the one or more programs further comprise an opening module that controls the display screen to turn on when the display screen has been turned off more than a second predefined time.

5. The electronic device as described in claim 1, wherein the one or more programs further comprise a first detecting module that detects a reading time of eyes of the user by calculating a time difference between a current system time of the electronic device and the initial time, and determines whether the user keeps looking at the display screen not less than the first predefined time according to the reading time of the eyes.

6. A method being executed by a processor of an electronic device for relieving visual fatigue, comprising:
    controlling a visual sensor of the electronic device to capture an image of eyes of a user;
    detecting whether the user is looking at a display screen of the electronic device by determining whether the image of the eyes matches an eyes models stored in a storage system of the electronic device;
    adjusting a font size of a font displayed on the display screen to a preset font size when the user is looking at the display screen; and
    prompting the user to have a rest and control the display screen to turn off when the user has looked at the screen not less than a first predefined time.

7. The method as described in claim 6, further comprising: determining that the user is looking at the display screen when the image of the eyes matches one of the eyes models.

8. The method as described in claim 6, further comprising: setting an initial time when the visual sensor determines that the user is looking at the display screen.

9. The method as described in claim 6, further comprising: turning on the display screen automatically when the screen has been turned off more than a second predefined time.

10. The method as described in claim 7, further comprising detecting a reading time of eyes of the user by calculating a time difference between a current system time of the electronic device and the initial time; and determining whether the user keeps looking at the display screen not less than the first predefined time according to the reading time of the eyes.

11. A non-transitory storage medium having stored thereon instructions that, when executed by a processor, cause the processor to perform a method for relieving visual fatigue of using the electronic device, the method comprising:

controlling a visual sensor of the electronic device to capture an image of eyes of a user;

detecting whether the user is looking at a display screen of the electronic device by determining whether the image of the eyes matches an eyes models stored in a storage system of the electronic device;

adjusting a font size of a font displayed on the display screen to a preset font size when the user is looking at the display screen; and prompting the user to have a rest and control the display screen to turn off when the user has looked at the screen not less than a first predefined time.

12. The non-transitory storage medium as described in claim 11, further comprising:

determining that the user is looking at the display screen when the image of the eyes matches one of the eyes models.

13. The non-transitory storage medium as described in claim 11, further comprising:

setting an initial time when the visual sensor determines that the user is looking at the display screen.

14. The non-transitory storage medium as described in claim 11, further comprising:

turning on the screen when the screen has been turned off more than a second predefined time.

15. The non-transitory storage medium as described in claim 11, further comprising:

detecting a reading time of eyes of the user by calculating a time difference between a current system time of the electronic device and the initial time; and determining whether the user keeps looking at the display screen not less than the first predefined time according to the reading time of the eyes.

* * * * *